United States Patent [19]

Allcock et al.

[11] 4,321,217

[45] Mar. 23, 1982

[54] DIALKYLATED PHOSPHAZENE OLIGOMERS AND METHOD OF PREPARATION THEREOF

[75] Inventors: Harry R. Allcock; Paul J. Harris, both of State College, Pa.

[73] Assignee: The United States of America as represented by the Secretary of the Navy, Washington, D.C.

[21] Appl. No.: 156,714

[22] Filed: Jun. 5, 1980

[51] Int. Cl.$^3$ .............................. C07F 9/65; C07F 9/56
[52] U.S. Cl. ............................... 260/543 PN; 526/276
[58] Field of Search .................................... 260/543 PN

[56] References Cited

FOREIGN PATENT DOCUMENTS 667557  6/1979  U.S.S.R. ........................ 260/543 PN

*Primary Examiner*—Paul J. Killos

*Attorney, Agent, or Firm*—R. S. Sciascia; A. L. Branning; T. E. McDonnell

[57] ABSTRACT

Di-alkylated phosphazene oligomers of the general formula: $(NP(X_2))_n NPRR'$ wherein X represents chloride, bromide, or iodide, R and R' represent a linear or branched, saturated or unsaturated hydrocarbon and n represents an integer from 2 to 8, are prepared by reacting, in a nonoxidizing atmosphere, a perhalopolyphosphazene, a Grignard reagent and a cuprous complex in solution, followed by the addition of alkyl iodide or an activated alkyl halide. Polymers, useful as high-temperature elastomers, are prepared from the above oligomers by heating them at a temperature from about 200° C. to about 300° C., followed by a reaction with an amine, metal alkoxide, or a metal aryloxide at a temperature from 20° C. to 200° C.

7 Claims, No Drawings

DIALKYLATED PHOSPHAZENE OLIGOMERS AND METHOD OF PREPARATION THEREOF

BACKGROUND OF THE INVENTION

The present invention pertains generally to the synthesis of phosphazene oligomers and polymers and in particular to the dialkylation of these oligomers and polymers.

Alkylation of phosphazene oligomers is of particular importance for improvements in thermal stability, glass-transition temperature, degree of crystallinity and melt behavior of polyphosphazenes polymerized from these oligomers. These polymers are becoming increasingly important because of the flexibility, flame retardation, and resistance to ultraviolet light at temperatures above 200° C. Furthermore, the decomposition temperature of these polymers, being in excess of 200° C., constitutes a significant improvement over organic polymers.

It has been determined that the hydrogen-phosphorous bond is the least stable bond in these compounds. Consequently, attempts have been made to replace the hydrogen atom with other substituents. Limited success has been met in substituting alkoxy or aryl groups on the phosphorus atom. An example of an alkoxy substitution on the phosphorus atom is found in H. R. Allcock et al., J. Amer. Chem. Soc., 99 6095-6 (1977). In C. W. Allen et al., Inorg. Chem. 7, 2177-83 (1968), a method for synthesizing aryl-substituted phosphazene fluoride is described.

Attempts to directly bond alkyl groups to the phosphorus atom of polyphosphazenes through carbon-phosphorus bonds have, on the whole with one exception, been unsuccessful. Generally, they proceed by a reaction of a Grignard or organo-lithium reagent with poly(dichlorophosphazenes). These attempts result in cleavage reactions due to the preference of these reagents to degrade the phosphazene skeleton in preference to replacement of the halogen. See, for example, C. F. Liu, R. L. Evans, U.S. Pat. No. 3,169,933 issued in 1965 and J. R. Callum et al., J. Polym. Sci., part A-1, 6 3163-5 (1968).

The only successful alkylation of the phosphorus atom of a polyphosphazene is reported in P. J. Harris and H. R. Allcock, J. Amer. Chem. Soc., 100:20 6512-3 (1978). This method proceeds by reacting a hindered alcohol with the organo-copper intermediate formed by the reaction of a poly(dichlorophosphazene), a Grignard agent, and [n-Bu$_3$PCuI]$_4$. The product so produced has only a single alkyl group on the phosphorus atom, leaving a thermally and hydrolytically unstable hydrogen-phosphorus bond. While these polymers had a reasonably high decomposition temperature, approximately 200° C., the hydrolytic instability of the remaining phosphorus-hydrogen bonds limited these polymers for uses in totally dry environments.

SUMMARY OF THE INVENTION

It is therefore an object of the present invention to synthesize phosphazene oligomers and polymers with excellent thermal and hydrolytic stabilities.

A further object is to bond two alkyl groups directly onto the phosphorus atom of polyphosphazene through carbon-phosphorus bonds without appreciable chain or ring cleavage.

Another object of the present invention is to produce diakylated polyphosphazene in high yields at a reasonable cost.

These and other objects are achieved by an electrophilic attack of an alkyl halide on the organo-copper intermediate formed by reacting poly(dichlorophosphazene), a Grignard agent, and [n-Bu$_3$PCuI]$_4$.

DETAILED DESCRIPTION OF INVENTION

The oligomers of the present invention, termed 1,1,-dialkylperhalopolyphosphazenes, can be cyclic or acyclic, and have the general formula $(NP(X_2))_n NPRR'$, wherein X represents chloride or bromide; R and R' represent linear or branched, saturated or unsaturated hydrocarbons having from 1 to 15 carbon atoms in the backbone chain and preferably having two to five carbon atoms with 1 to 30 side chains of 1 to 4 carbon atoms and preferably from 2 to 6 side chains of 1 to 3 carbon atoms; and n represents an integer from 2 to 8.

The oligomers and the corresponding polymers preferred by consideration of cost, availability of starting materials, yields are 1,1,-dialkyl-tetrachlorocyclotriphosphazene, and 1,1,-diakylhexachlorocyclotetraphosphazene, wherein the alkyl groups are ethyl, propyl, and butyl.

The exact reaction pathway leading to the formation of the metallo-phosphazene intermediate is not completely known, but experimental data indicate that the following mechanism, represented by a preparation involving hexachlorocyclotriphosphazene, is the overall reaction mechanism.

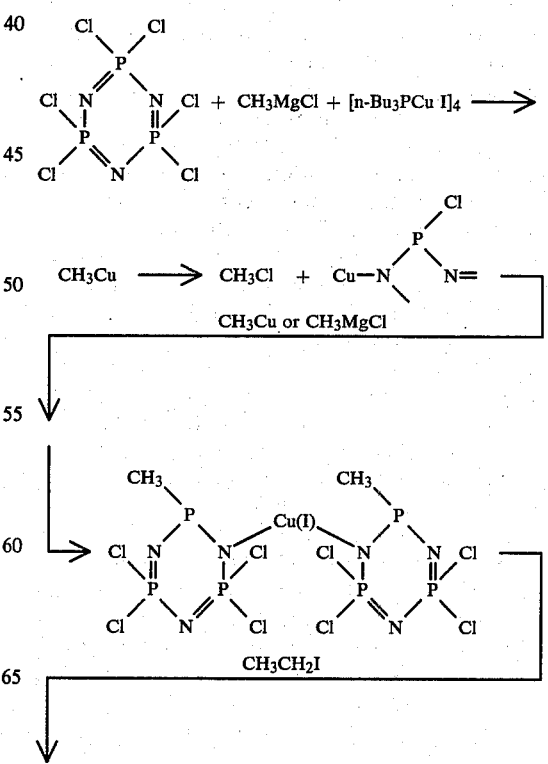

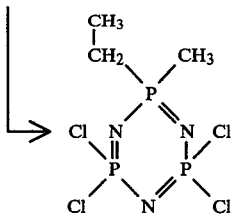

The synthesis begins by admixing in a solvent under a non-oxidizing atmosphere perchloropolyphosphazene and a cuprous complex in a phosphazene-to-copper mole ratio from about 4:1 to about 8:1 and preferably 8:1 at a temperature not exceeding the decomposition temperature of the alkyl copper intermediate. Examples of suitable cuprous complexes are copper iodide (CuI) and trialkyl phosphine copper halide tetramer $R_3PCuX_4$, wherein, R represents-methyl, ethyl, propyl, butyl, or pentyl and X represents iodide, bromide, or chloride. The solvent must at least completely dissolve the metallo-phosphazene intermediate and have electron-donor characteristics and preferably dissolve all reactants. The preferred solvents are tetrahydrofuran, ethyl ether, and propyl ether. The decomposition temperature of the alkyl-copper intermediate can be readily determined by reference to a standard data book. Tertiary alkyl copper compounds are the most unstable and therefore the synthesis is run at $-80°$ C. Primary alkyl copper compounds are the most stable, allowing the synthesis to occur at $0°$ C. The reaction can proceed as low as $-100°$ C. at an adequate reaction rate.

As the phosphazene and the copper reagent are being stirred, the Grignard reagent is slowly added in a Grignard-to-copper mole ratio from about 24:1 to about 40:1 and preferably 24:1 at a rate which keeps the temperature and reaction under control. Since the production and consumption of the copper alkyl intermediate are almost instantaneous, the temperature can be allowed to rise to about room temperature. In fact, the temperature can be raised to about $40°$ C. Mixing the reactants is continued until the reaction forming the metallo-phosphazene intermediate is complete as determined by, e.g., monitoring the reaction solution with NMR.

The second alkyl group (R') on the phosphorus comes from an alkyl iodide or an activated alkyl halide (R'X) wherein R' and X are defined as before. An activated alkyl halide is one which forms a stabilized, unhindered carbonium ion. This information can be obtained by reference to standard tests. Examples of activated alkyl halides are allyl halides or propargyl halides. The alkyl iodide or activated alkyl halide is added to the reaction mixture at a temperature from about $-20°$ C. to about $50°$ C. and preferably at $25°-30°$ C. in an amount at least two times greater than the amount of phosphazene reactant and preferably from 4 to 5 times greater. Stirring is continued until the reaction is complete, usually about three days. The completion can be determined by monitoring the reaction solution with NMR. Considerable care must be taken in isolating the product because of the possibility of side reactions, especially hydrolysis, which result in decomposition of the products.

The preferred method of isolation comprises removing the solvent, e.g., tetrahydrofuran by reduced pressure, dissolving the reaction mixture in toluene or benzene or similar organic polar solvent which is immiscible with water but which dissolves the reaction mixture; washing the solution with at least an equal volume of 10 to 35% aqueous HCl or acetic acid or any aqueous non-oxidizing acid until two layers (organic and inorganic) become fully developed, generally requiring from 5 to 10 minutes; drying the organic layer with a standard drying agent, e.g., $CaCl_2$, $MgSO_4$, $Na_2SO_4$, or alumina; and removing the solvent by, e.g., vacuum. The temperature during isolation is, of course, above the freezing points of the liquid reactants and solvents, but is not in excess of $35°$ C. and preferably $25°$ C. The upper limit on the temperature is necessitated by the ease with which hydrolysis occurs during the reaction. The possibility of hydrolysis also requires extreme caution during the washing step. If hydrolysis occurs, it can be reduced or eliminated by reducing the washing time, by reducing the temperature, or by using a weaker or more dilute acid.

The product is purified by dissolving the product in, e.g., $CH_2Cl_2$, filtering the solution through any standard material, e.g., alumina, recrystalizing from n-hexane or other similar nonpolar organic solvent.

This method was reported in P. J. Harris and H. R. Allcock in J. Chem. Soc., Chem. Commun., Aug. 1, 1979, on p. 714 which is incorporated herein by reference.

The following examples are given to illustrate the practice of the present invention. It is understood that the examples are given by way of illustration and are not meant to limit the specification or the claims to follow in any manner.

Hexachlorocyclotriphosphazene was supplied by the Ethyl Corporation and was purified by sublimation, followed by two recrystallizations from n-hexane. The Grignard reagents were commercial products obtained from Aldrich or Alfa-Ventron. Tetrahydrofuran was distilled into the reaction flask under an atmosphere of dry nitrogen from a sodium-benzophenone ketal drying agent. The reagent, $[n-Bu_3PCuI]_4$, was prepared by the method disclosed in G. B. Kauffman and L. A. Teter, Inorg., Synth., I, 9 (1963) and was recrystallized from 2-propanol/ethanol before use. All reactions were carried out under an atmosphere of dry nitrogen.

EXPERIMENTAL SECTION I

General Synthesis of dialkyltetrachlorocyclotriphosphazenes of Table I

Hexachlorocyclotriphosphazene (HCCTP) (5.0 g, 14.37 mmol) and $[n-Bu_3PCuI]_4$ (4.0 g, 2.53 mmol) were stirred in tetrahydrofuran (150 ml) at $-80°$ C., and the Grignard reagent (56 mmol) was then added dropwise. The reaction mixture was allowed to warm slowly to $25°$ C. and was then stirred for 14 hours to optimize the yield of the organo-copper intermediate.

The mixture was then cooled to $0°$ C., the alkyl halide (42 mmol) was added, and stirring was continued at $25°$ C. for an additional 20 hours. The product was generally isolated in more than 70% yield (based on the amount of HCCTP) after recrystallization from n-hexane. In some cases difficulty was experienced due to hydrolysis in the product-isolation process.

TABLE I

| Grignard Reagent | Organic Halide | Phosphazene Substituents | |
|---|---|---|---|
| RMgCl | R'X | R | R' |
| CH₃MgCl | CH₂=CHCH₂Br | CH₃ | —CH₂CH=CH₂ |
| CH₃MgCl | CH₂—CH=CH—CH₂Br | —CH₃ | —CH(CH₃)—CH=CH₂ |
| CH₃MgCl | CH≡C—CH₂Br | —CH₃ | —CH=C=CH₂ |
| CH₃CH₂MgCl | CH₃I | —CH₂CH₃ | —CH₃ |
| CH₃(CH₂)₂MgCl | CH₃I | —(CH₂)₂CH₃ | —CH₃ |
| CH₃(CH₂)₃MgCl | CH₃I | —(CH₂)₃CH₃ | —CH3 |
| (CH₃)₂CHMgCl | CH₂=CH—CH₂Br | —CH(CH₃)₂ | —CH₂—CH=CH₂ |
| (CH₃)₃CMgCl | CH₂=CH—CH₂Br | —C(CH₃)₃ | —CH₂—CH=CH₂ |
| CH₂=CH—CH₂MgCl | CH₃I | —CH₂—CH=CH₂ | —CH₃ |
| CH₂=CH—CH₂MgCl | CH₂=CH—CH₂Br | —CH₂—CH=CH₂ | —CH₂—CH=CH₂ |

EXPERIMENTAL SECTION II

Proof of Structure

The structures of 1,1-dialkyltetrachlorocyclotriphosphazene compounds of this invention were determined by the use of a combination of infrared and $^1H$, $^{13}C$ and $^{31}P$ NMR spectroscpy, mass spectrometry, (low and high resolution) and in representative cases, elemental analysis. These data are listed in Table II–VI for two compounds of Table I.

All of these compounds displayed a strong parent ion in the mass spectrum with a characteristic $Cl_4$ isotope pattern. The mass spectral data for these compounds are listed in Table II.

The overall structure of the phosphazene ring in the compounds was determined using a combination of infrared and $^{31}P$ NMR spectroscopy. The infrared spectra of the compounds displayed an intense absorbance between 1100 and 1300 $cm^{-1}$, a characteristic of the PN skeleton in all phosphazene compounds. Other bands in the infrared spectrum were assigned to C—H, P—C, (C=C), and P—Cl vibrations. All these data and tentative assignments are listed in Table III.

The $^{31}P$ NMR spectra of the compounds (listed in Table IV could be interpreted as simple $AB_2$ spin systems. The position of resonance assigned to the phosphorus atom bound to the alkyl groups appeared as a triplet, centered between 35.7 and 54.8 ppm. This assignment was confirmed from the proton undecoupled $^{31}P$ NMR spectrum, where only this resonance broadened, due to unresolved proton-phosphorus couplings. The other resonance in the spectrum, assigned to the $PCl_2$ group, remained virtually unchanged.

The position of resonance assigned to the two phosphorus atoms bound to chlorine always appeared as a doublet, centered between 17.7 and 19.3 ppm. The position of this resonance is shifted upfield from the position of resonance observed for the phosphorus nuclei in hexachlorocyclotriphosphazene, which was found to occur at 19.8 ppm. This greater shielding is presumably due to the presence of the alkyl group in the compounds.

The nature of the alkyl group bound to the phosphazene ring in the compounds was determined using a combination of $^1H$ and $^{13}C$ NMR spectroscopy. In many cases the $^1H$ NMR spectra (listed in Table V) consisted of a complex pattern of overlapping resonances that could not be readily interpreted. However, the $^{13}C$ NMR spectra (listed in Table V) were, in most cases, well resolved, first order spectra, from which the position of resonance of every carbon atom and a value for each P—C coupling constant could be determined. The carbon atoms bound directly to the phosphazene ring always appeared as a doublet of triplets, due to coupling to the near ($J_{PC}$) and the remote ($J_{PNPC}$) phosphorus atoms, Carbon atoms 2 or 3 bonds removed from the phosphazene ring appeared as doublets, coupled only to the near phosphorus nucleus. All the peak assignments and coupling constants are listed in table VI.

TABLE II

Dialkyphosphazenes. Characterization Data

| Compound | % Yield | Mp. (C.°) | mass spectral data | | elemental analysis data | | | |
|---|---|---|---|---|---|---|---|---|
| | | | found | calcd. | | found | | calcd. |
| N₃P₃Cl₄(n-C₄H₉)(i-C₃H₇) | 47 | 122 | 375 | 375 | | 374.9334 | | 374.9311 |
| N₃P₃Cl₄(C₃H₅)(CH₃) | 84 | 90 | 331 | 331 | C | 14.57 | C | 14.41 |
| | | | | | H | 2.37 | H | 2.40 |
| | | | | | N | 12.53 | N | 12.61 |
| | | | | | P | 27.78 | P | 27.92 |
| | | | | | Cl | 42.52 | Cl | 42.64 |

TABLE III

Dialkyl Phosphazenes Infrared Data. ($cm^{-1}$)

| Compound | C—H | P=N | P—C | P—Cl | Other |
|---|---|---|---|---|---|
| N₃P₃Cl₄(C₃H₅)(CH₃) | 3095 (w) | 1245 (s) | 1300 (s) | 585 (s) | 1640 (m)(C=C) |
| | 3070 (w) | 1205 (vs) | 805 (ms) | 505 (s) | 1020 (sh) |
| | 2990 (m) | 1195 (sh) | 750 (m) | 425 (m) | 990 (w) |
| | 2950 (w) | 1170 (vs) | 750 (ms) | | 930 (ms) |
| | 2020 (m) | 1145 (sh) | 645 (ms) | | 920 (ms) |
| | 2895 (w) | | | | 910 (s) |
| | 1420 (m) | | | | 870 (m) |
| | 1400 (sh) | | | | 830 (w) |
| | 1390 (mw) | | | | |
| N₃P₃Cl₄(n-C₄H₉)(iC₃H₇) | 2970 (m) | 1210 (vs) | 1270 (m) | 585 (s) | 1105 (mw) |
| | 2945 (m) | 1175 (vs) | 1240 (s) | 520 (s) | 1040 (w) |
| | 2885 (w) | 1150 (sh) | 820 (mw) | 460 (w) | 1015 (vw) |

TABLE III-continued

| Compound | Dialkyl Phosphazenes Infrared Data. (cm$^{-1}$) | | | | Other |
|---|---|---|---|---|---|
| | C—H | P=N | P—C | P—Cl | |
| | 1475 (m) | | 765 (vw) | 340 (w) | 940 (vw) |
| | 1465 (mw) | | 755 (mw) | | 910 (mw) |
| | 1410 (vw) | | 725 (w) | | 900 (sh) |
| | 1395 (w) | | 690 (w) | | 880 (vw) |
| | 1375 (vw) | | 635 (ms) | | 830 (m) |
| | 1310 (w) | | | | |

TABLE IV

Dialkyl Phosphazerns - $^{31}$P NMR Data

| Compound | Chemical shift. (ppm) | | Coupling Constend $J_{PNP}$(Hz) |
|---|---|---|---|
| | P(R)$_2$ | P(Cl)$_2$ | |
| N$_3$P$_3$Cl$_4$(n-C$_4$H$_9$)(i-C$_3$H$_7$) | 51.1 (t) | 19.0 (d) | 4.3 |
| N$_3$P$_3$Cl$_4$(C$_3$H$_5$)(CH$_3$) | 36.9 (t) | 18.5 (d) | <2 |

Table V

Dialkylphosphazenes $^1$H NMR Data

| Compound | Chemical Shift ( ) | Coupling Constens (Hz) |
|---|---|---|
| N$_3$P$_3$Cl$_4$(n-C$_4$H$_9$)(i-C$_3$H$_7$) | —(CH$_2$)$_3$CH$_3$ 1.6 (br, m) | unresolved |
| | —(CH$_2$)$_3$CH$_3$ 0.85 (t) | $J_{HCCH}$ = 7.0 |
| | —CH(CH$_3$)$_2$ 1.9 (br, m) | unresolved |
| | —CH(CH$_3$)$_2$ 1.10 (d, d) | $J_{PCCH}$ = 20.0 $J_{HCCH}$ = 7.1 |
| N$_3$P$_3$Cl$_4$(C$_3$H$_5$)(CH$_3$) | —CH$_2$CH=CH$_2$ 2.7 (br, m) | unresolved |
| | —CH$_2$CH=CH$_2$ 5.5 | unresolved |
| | —CH$_3$ 1.66 (d, t) | $J_{PCH}$ = 14.5 $J_{PNPCH}$ = 2.1 |

TABLE VI

Dialkylphosphazenes $^{13}$C NMR Data

| Compound | Chemical Shift (ppm) | Coupling Constants (Hz) |
|---|---|---|
| N$_3$P$_3$Cl$_4$(n-C$_4$H$_9$)(i-C$_3$H$_7$) | —CH$_2$CH$_2$CH$_2$CH$_3$ 28.06 (d, t) | $J_{PC}$ = 87.5 $J_{PNPC}$ = 3.3 |
| | —CH$_2$CH$_2$CH$_2$CH$_3$ 22.85 (d) | $J_{PCC}$ = 5.5 |
| | —CH$_2$CH$_2$CH$_2$CH$_3$ 23.38 (d) | $J_{PCCC}$ = 15.5 |
| N$_3$P$_3$Cl$_4$(C$_3$H$_5$)(CH$_3$) | —CH$_2$CH=CH$_2$ 37.44 (d, t) | $J_{PC}$ = 87.8 $J_{PNPC}$ = 2.7 |
| | —CH$_2$CH=CH$_2$ 124.75 (d) | $J_{PCC}$ = 11.7 |
| | —CH$_2$CH=CH$_2$ 120.88 (d) | $J_{PCCC}$ = 13.6 |

Compounds with the following formula: [NP(Y$_2$)$_n$NPRR']$_m$ wherein Y represents chloride, bromide, alkoxy, aryloxy, or amino groups, n is defined as before, and m is an average value and equals any value up to about 15,000, can be prepared from the subject oligomers by standard techniques. The alkoxy group has from 1 to 8 carbon atoms in the backbone chain and from 1 to 4 carbon atoms in any branch. The aryloxy derivative has from 6 to 10 carbon atoms. The alkoxy and aryloxy groups may be substituted with halide, nitro, or cyano group, but the preferred substituent is fluoride. The amino group has from 1 to 8 carbon atoms and can be either a primary or secondary amine. An excellent technique for this polymerization is described in U.S. Pat. No. 3,370,020 issued Feb. 20, 1968 on U.S. patent application Ser. No. 400,222 to H. R. Allcock and R. L. Kugel. The polymer has only halogen substituted which can be converted to oxy or amino substituents by standard techniques such as the ones described in U.S. Pat. No. 3,370,020 or in Allcock, H. R. *Inorganic Polymers* in Sci. American pp. 66–74, March 1974.

EXPERIMENTAL SECTION III

Polymerization of (NP(Cl$_2$))$_2$NP(CH$_3$)$_2$

Five grams of 1,1-dimethyltetrachlorotriphosphazene were placed in a sealed tube and heated to 250° C. The viscosity was monitored by visual inspection. After fifteen hours, the material was almost solidified, whereupon, the material was removed from the oven. The tube was opened and the contents were refluxed in 100 ml of tetrahydrofuran with sodium trifluoroethoxide prepared from 20 grams of sodium reacting with 100 ml of trifluoroethanol in 500 ml of tetrahydrofuran for two days. The progress of the reaction was monitored by the $^{31}$P n.m.r. bandshift.

Upon completion, the contents were poured into two liters of chilled water. The product was separated by filtration.

The product was brown in appearance and was elastomeric. The molecular weight was determined to be 5 × 10$^5$. A sample of the product (2.0 gm) was heated at 200° C. in a humid atmosphere for 24 hours without any loss in weight.

The stability of the polymer in a humid atmosphere demonstrates the advancement of the present oligomers and polymers over those reported in P. J. Harris and H. R. Allcock, J. Amer. Chem. Soc., 100:20 6512-3 (1978). Although processing is more difficult, these oligomers and polymers represent a major improvement over the other oligomers and polymers.

Obviously many modifications and variations of the present invention are possible in light of the above teachings. It is therefore to be understood that within the scope of the appended claims the invention may be practiced otherwise than as specifically described.

What is claimed is:

1. A phosphazene oligomer having the formula: (NP(X$_2$))$_n$NPRR', wherein X is selected from the group consisting of chloride, and bromide, R and R' represent a linear or branched or saturated or unsaturated hydrocarbon, and n represents an integer from 2 to 8.

2. The phosphazene oligomer of claim 1 wherein said oligomer is cyclic.

3. The oligomer of claim 2 wherein r is a linear alkyl and has from 1 to 15 carbon atoms.

4. The oligomer of claim 2 wherein R is a branched alkyl, has 1 to 15 carbon atoms in the backbone chain, and has from 1 to 30 side chains of 1 to 4 carbon atoms.

5. A method for alkylating phosphazene oligomers which comprises:

admixing, in a solvent, perhalopolyphosphazene and a cuprous complex in a phosphazene-to-copper ratio from about 4:1 to about 8:1 in a nonoxidizing atmosphere;

adding, while maintaining mixing, a Grignard reagent in a Grignard-to-copper mole ratio from about 24:1 to about 40:1;

mixing the reactants until a metallo-phosphazene intermediate is formed;

adding an alkyl iodide or activated alkyl halide to said intermediate in an alkyl-intermediate mole ratio of at least 2:1 while mixing is continued;

mixing the mixture until the reaction is complete; and isolating the product.

6. The method of claim 5 wherein said alkyl iodide or activated alkyl halide is added to intermediate in an alkyl-intermediate mole ratio from about 4:1 to 5:1.

7. The method of claim 6 wherein said product is isolated by the method which comprises forming a solution of the reaction mixture in an organic polar solvent, washing said solution with about 30 percent aqueous acid, allowing an organic layer and an inorganic layer to fully develop, drying said organic layer and removing the solvent of the washed organic layer by vacuum.

* * * * *